US009629638B2

(12) United States Patent
Mootien et al.

(10) Patent No.: US 9,629,638 B2
(45) Date of Patent: Apr. 25, 2017

(54) SAW, A SAW BLADE, A CONNECTION MECHANISM AND ASSOCIATED METHODS

(71) Applicant: DePuy Synthes Products, Inc., Raynham, MA (US)

(72) Inventors: Azagen Mootien, Oberdorf (CH); Daniel Herzog, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 657 days.

(21) Appl. No.: 13/937,267

(22) Filed: Jul. 9, 2013

(65) Prior Publication Data

US 2014/0018811 A1 Jan. 16, 2014

Related U.S. Application Data

(60) Provisional application No. 61/670,914, filed on Jul. 12, 2012, provisional application No. 61/692,869, filed on Aug. 24, 2012.

(51) Int. Cl.
| | |
|---|---|
| *B23D 61/00* | (2006.01) |
| *B23B 19/00* | (2006.01) |
| *A61B 17/14* | (2006.01) |
| *B27B 19/00* | (2006.01) |
| *B27B 5/30* | (2006.01) |

(52) U.S. Cl.
CPC .......... *A61B 17/141* (2013.01); *A61B 17/148* (2013.01); *B23D 61/006* (2013.01); *B27B 5/30* (2013.01); *B27B 19/008* (2013.01); *Y10T 29/49815* (2015.01); *Y10T 83/04* (2015.04)

(58) Field of Classification Search
CPC ... B27B 19/008; B27B 19/006; B23D 49/006; A61B 17/148
USPC ...................... 606/82, 178; 30/369, 392–394
See application file for complete search history.

(56) References Cited

U.S. PATENT DOCUMENTS

| | | | | |
|---|---|---|---|---|
| 5,697,158 A | * | 12/1997 | Klinzing | ................ A61B 17/14 30/166.3 |
| 5,846,244 A | * | 12/1998 | Cripe | ..................... A61B 17/14 30/166.3 |
| 5,916,218 A | | 6/1999 | Hagen et al. | |
| 6,007,541 A | | 12/1999 | Scott | |
| 2014/0068952 A1 | * | 3/2014 | Soreo | ................... B27B 19/008 30/369 |

(Continued)

FOREIGN PATENT DOCUMENTS

DE 19614832 4/1997

OTHER PUBLICATIONS

International Search Report issued in PCT/US2013/049632 dated Oct. 16, 2013, 4 pgs.

(Continued)

*Primary Examiner* — David Bates
(74) *Attorney, Agent, or Firm* — Baker & Hostetler LLP

(57) ABSTRACT

The present disclosure relates to a saw, comprising a drive, a first blade configured to oscillate about an axis perpendicular to a plane defined by a surface of the first blade, a second blade configured to oscillate about an axis perpendicular to the plane in a direction opposite to that of the first blade, and wherein gearing is provided between the drive and the first and second blades to reduce the speed transmitted from the drive to the blades. A saw blade, a connection mechanism for connecting a blade to a saw and associated methods are also provided.

33 Claims, 6 Drawing Sheets

(56) References Cited

U.S. PATENT DOCUMENTS

2014/0182872 A1* 7/2014 Rubens ............... B27B 19/006
173/213

OTHER PUBLICATIONS

International Preliminary Report on Patentability issued in PCT/US2013/049632 dated Jan. 13, 2015, 8 pgs.

* cited by examiner

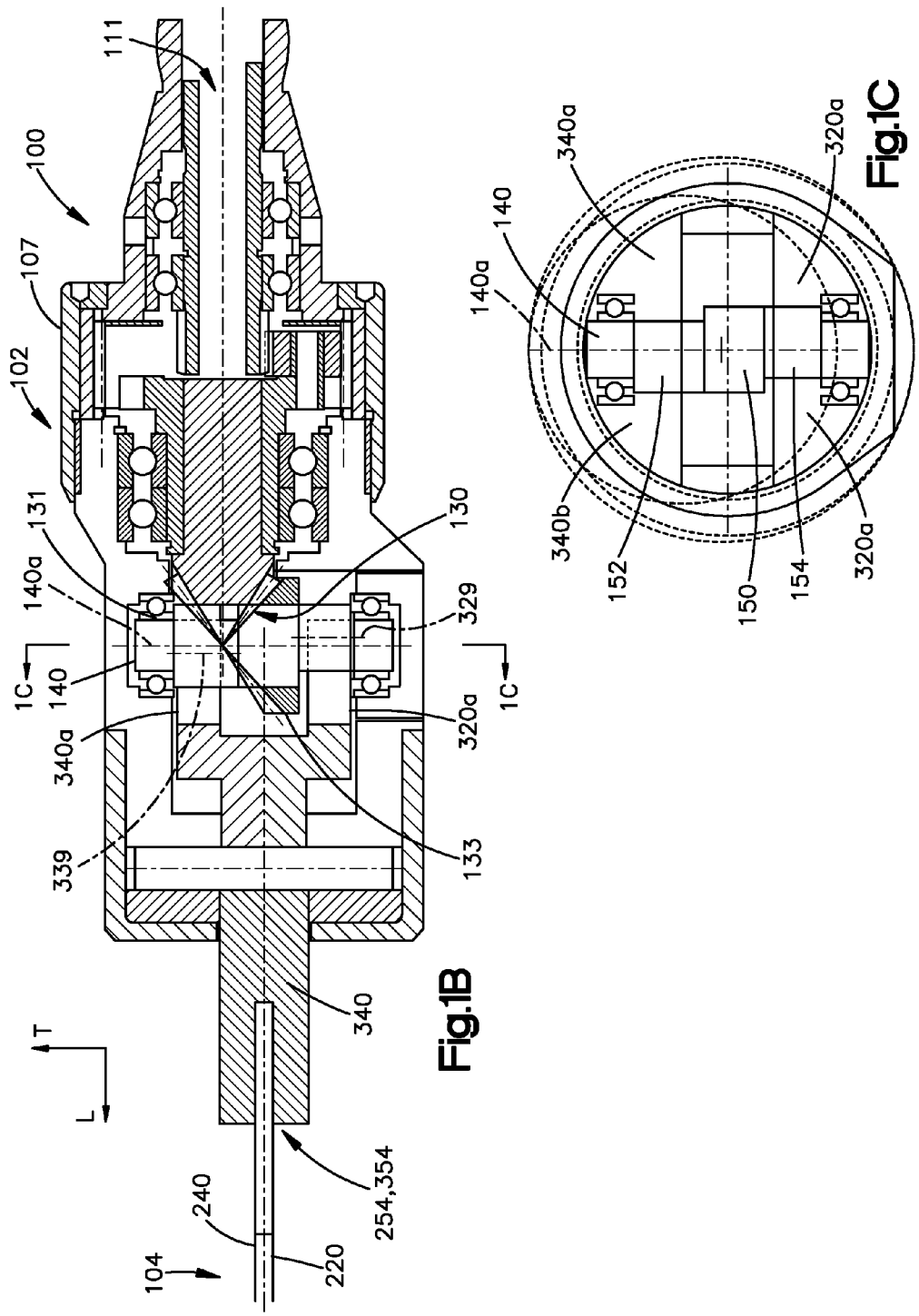

SAW, A SAW BLADE, A CONNECTION MECHANISM AND ASSOCIATED METHODS

CROSS-REFERENCE TO RELATED APPLICATIONS

This application claims benefit to U.S. Provisional Patent Application Ser. No. 61/670,914 filed on Jul. 12, 2012 and U.S. Provisional Patent Application Ser. No. 61/692,869 filed on Aug. 24, 2012, the entire disclosures of each application is herein incorporated by reference for all purposes.

TECHNICAL FIELD

The present disclosure relates to saw blades, a connection mechanism for connecting a saw blade to a saw, a saw, a method of cutting and a method of removing saw blades from a saw.

BACKGROUND

Powered saws are often used in surgical procedures, particularly osteotomies. It is desirable to apply a high torque to the bone by the blades of a saw during the cutting procedure to improve the precision of the cutting and reduce the time it takes to perform the procedure. In addition, cutting efficiency can be affected by the frequency of oscillation of the saw blades, if the frequency of the saw is similar to that of the bone, cutting performance would be zero. U.S. Pat. No. 5,846,244 discloses a counter-balanced oscillating saw in which the momentum produced by one blade is offset by momentum produced by its counterpart cutting blade to reduce mechanical vibration, rotational and linear movement of the saw.

The blades of surgical saws are often used in sterile environments. It is useful to be able to provide disposable blades or blades that can be processed for reuse independently of the saw so that a saw can be reused while avoiding the expense or time of sterilizing the whole saw. However, it is important that any blade is securely connected to the handpiece during use to avoid the highly unsatisfactory consequences of the blades becoming loose during a cutting procedure. Therefore, it is desirable to provide an independent blade which is easily removable from the saw for processing but which can be securely connected to the saw during use.

There is thus a need to provide an improved saw which can cut using high torque and prevents the object to be cut oscillating in harmony with the saw, and blades which are independent of the saw but can be securely connected to the saw.

SUMMARY

In a first aspect of the present disclosure there is provided a saw blade that includes a cutting edge at a distal end thereof. The saw blade can have an attachment portion at a proximal end of the blade that is configured to connect the blade to a saw, and a projection that extends from the blade and is resiliently biased into a position in which it extends away from a surface of the blade. The saw blade can be configured to cut bone. The attachment portion and the projection act can act in tandem to allow the blade to be removably connected to the saw. The projection may be positioned towards the proximal end of the blade. The projection may be integral to the blade. Alternatively, the projection may be a separate component fixed to the blade. In an embodiment, the attachment portion comprises a spanner shaped head. The attachment portion can also comprise a pair of arms that are substantially parallel with respect to each other. The spanner shape head and the pair of arms can define an inner surface that extends along an angle of between about 45° and about 75° relative to a plane of the blade. In the exemplary embodiment, the angle can be about 60°. When the attachment portion is configured in this way, the attachment portion of the blade can be connected to a complementarily angled surface to provide an interlock thereto.

In a second aspect of the present disclosure there is provided a connection mechanism for connecting a saw blade to a saw. The connection mechanism can include a mounting member, for instance a mounting portion, that defines a receiving surface and a raised portion. The blade can define an opening that extends through the blade. The blade can define a surface that can be slid into engagement with the receiving surface. The raised portion is can be received by the opening of the blade. Engagement between the opening and the raised portion can prevent undesirable relative axial, i.e., longitudinal movement of the blade with respect to the saw. Thus, the blade is configured to securely connect to the raised portion of the mounting portion without the need for additional components. In an embodiment, the blade can define an inner surface that defines the opening. Further, the raised portion can define an outer surface. The opening inner surface and the outer surface of the raised portion can be complementarily angled so as to provide an interlock between the blade and the raised portion of the mounting portion. The interlock can prevent relative axial or longitudinal movement of the blade, which, although it may may cause vibrations between the surfaces of the blades (for instance when two blades are used) allows the blade to be slid into connection with the saw. In an embodiment, the opening inner surface may extend at an angle of between 45° and 75° relative to the plane of the blade. The angle of the opening inner surface relative the plane of the blade is about 60°.

As noted above, the blade may comprise two substantially parallel arms that at least partially define the opening. The configuration of the arms permits the blade to be slid easily into connection with the saw. The blade may also comprise a latching projection that extends into a latching surface in the mounting portion to prevent removal of the blade from the mounting portion or saw. The latching projection can be resiliently biased into a position extending away from the plane of the blade. And as a result, the latching projection can be biased into the position in which it extends into the latching surface. Thus, the blade can besecurely connected to the mounting portion once it has been slid into engagement with the receiving surface thereof.

The blade according the second aspect of the present disclosure may be the saw blade according to the first aspect of the present disclosure.

The saw may be a motor driven saw, a pneumatically driven saw or a manually driven saw.

In a third aspect of the present disclosure, there is provided a saw that includes a drive, a first blade configured to oscillate about an axis that is perpendicular to the plane defined by a surface of the blade. The saw can include a second blade configured to oscillate about an axis that is perpendicular to the plane in a direction opposite to that of the first blade. The axes can be the same, or each axis can be different. The gearing is disposed between the drive and the first and second blades and is configured to reduce the speed transmitted from the drive to the blades. The axes can be similar. The saw is thus configured to gear up the torque transferred to the blade from the drive. The increased torque output at the blades acts to perform the cut, while the blades oscillating in opposite direction reduces countertorque, which can prevent the object to be cut oscillating in harmony with the saw. The saw may further comprise an eccentric drive shaft rotatably connected to the drive, wherein the eccentric drive shaft acts to cause the first and second blades to oscillate. The eccentric drive shaft may be disposed perpendicular to the plane of each blade. The configuration of the eccentric drive shaft allows symmetrical design of the saw.

The gearing may comprise at least one gear, for instance a 90° gear transmission. The 90° gear allows the drive to be disposed parallel with the plane of the blade. The 90° gear transmission can provide a gear ratio of 1:1.5. Further, the speed of oscillation of the blades may be between 7000 to 10000 rpm, or 8000 to 10000 rpm. In an exemplary embodiment, the speed of oscillation of the blades is about 7000 rpm. Although the saw may function at lower speeds, for example 2000 to 3000 rpms, there is a tendency among surgeons to apply considerable pressure to the bone using the saw. At lower saw speeds, this tendency limits the ability of the saw. Operating the saw at oscillation speeds of 7000 rpm compensates for this tendency.

In an alternative embodiment, the gearing may comprise a planetary or a bevel gear. A planetary or bevel gear acts effectively to provide high torque at low speeds to the blades from the drive. In this embodiment, the 90° gear transmission may provide a gear ratio of 1:1.3846. The gearing can provide a gear ratio of 1:3.9474 and the speed of oscillation of the blades may be between 2000 to 3000 rpm. The gearing allows the blades to operate at lower speeds, thereby generating less heat.

The blades oscillate about the same axis. Further, the blades can be removably attached to the saw. Further, saw is designed to cut bone.

The blades can include first and second blades that comprise the blades of the first aspect of the present disclosure. The saw may further comprise a connection mechanism according to a second aspect of the present disclosure.

In a fourth aspect of the present disclosure there is provided a method of cutting comprising the step of transferring torque from a drive to first and second blades to oscillate the first and second blades in opposite directions relative to one another. The method includes the step of transferring the motion of the drive, via a gearing, so as reduce the speed transmitted from the drive to the first and second blades. The gearing increases the torque output to the blades from the drive, improving the blades cutting ability. Oscillating the first and second blades in opposite directions can prevent the object to be cut oscillating in harmony with the blades. The method may comprise the step of transferring torque from a drive to an eccentric drive shaft which causes the first and second blades to oscillate. The method may further comprise the step of transferring motion through a 90° gear transmission between the drive and the first and second blades. The method may also comprise the step of transferring motion via a planetary gear that is disposed between the drive and the blades. The drive may be a motor drive, a pneumatic drive or a manual drive. The method can include cutting bone.

In a fifth aspect of the present disclosure a method of removing saw blades from a saw is provided. The method comprises the step of moving a resiliently biased latch member of a blade from a first position in which it engages a mounting member of the saw to a second position in which it no longer engages the mounting member and removing the blade axially from the mounting member. The blade can be easily removed from the saw by sliding it out of engagement with a mounting member once a latch member has been moved from a latching position.

A sixth aspect of the present disclosure provides for use of a saw as described above in a procedure for cutting bone.

BRIEF DESCRIPTION OF THE DRAWINGS

The foregoing summary, as well as the following detailed description of illustrative embodiments of the devices and methods of the present application, will be better understood when read in conjunction with the appended drawings. For the purposes of illustrating the device and methods of the present application, there is shown in the drawings illustrative embodiments. It should be understood, however, that the application is not limited to the precise arrangements and instrumentalities shown. In the drawings:

FIG. 1B is a sectional side elevation view of a powered saw similar to the powered saw illustrated in FIG. 1A, but constructed in accordance with an alternative embodiment;

FIG. 1C is a side elevation view of an eccentric shaft of the powered saw illustrated in FIGS. 1A-B;

DETAILED DESCRIPTION OF ILLUSTRATIVE EMBODIMENTS

Figure 1A:
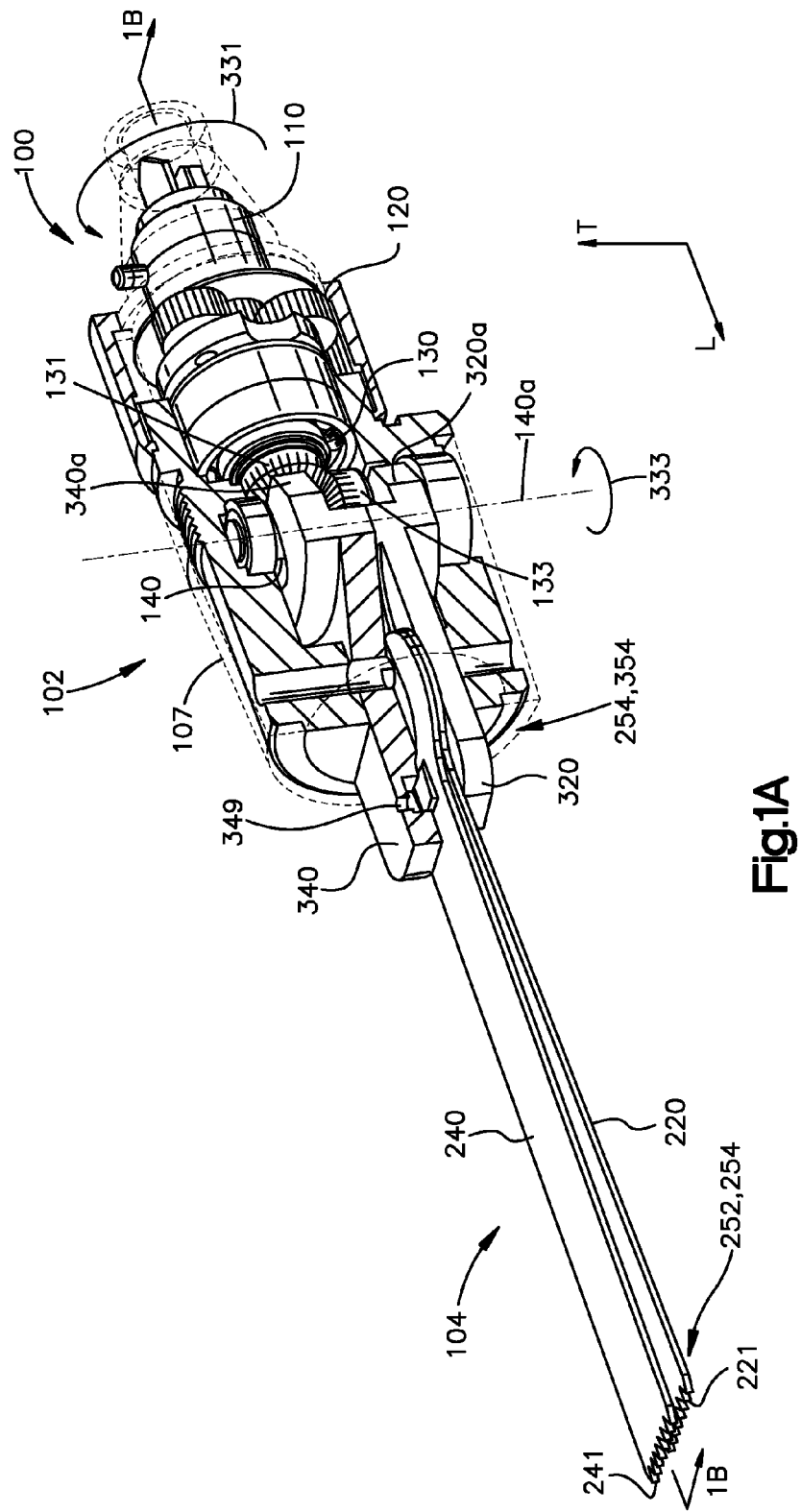
FIG. 1A is a cut-away perspective view of a powered saw according to an embodiment of the present disclosure.

Referring to FIG. 1A, a powered saw 100 having a drive location that is configured to support a motor drive 110 that is operably connected to eccentric shaft 140 via gearing. The powered saw 100 can include the motor drive 110, for instance at the drive location as illustrated in FIG. 1A, or the drive location can define a receptacle 111 (see FIG. 1B) that is configured to receive, for instance removably receive, a drive, such as a motor drive. The saw 100 can include a handle portion or handpiece 102 and a cutting portion 104 spaced from the handle portion 102 along the longitudinal direction L. The saw 100 can include a housing 107 for carrying at least a portion of the drive 110 and gearing. The housing 107 can at least partially define the receptacle 111.

The saw 100, or cutting portion 104, can include a first blade 220 and a second blade 240. The first and second blades 220 and 240 include proximal ends 252 and 352, respectively, each of which is configured to attach to the saw (detailed below), and distal ends 254 and 354, respectively, spaced from the proximal ends 252 and 352 along the longitudinal direction L when the blades are attached to the saw 100. The proximal ends of the blades can define respective blade attachment portions. The first blade 220 includes a first or upper surface 256 and a second or lower surface 258 spaced from the first surface 256 along the transverse direction T. The transverse direction T can be substantially perpendicular to the longitudinal direction L of the saw 100. The blades 220,240 can extend along the longitudinal direction L and have a transverse directional component. Further, the second blade 240 includes a first or upper surface 356 and a second or lower surface 358 spaced from the first surface 356 along the transverse direction T. Each respective blade surface extends between the proximal end 252,352 and the distal end 254,354 of the blades 220, 240, and can define the respective planes that extend along the longitudinal direction L. The blades 220, 240 each comprise a cutting portion 221, 241 disposed at the distal end 254, 354 thereof, which is positioned distal to the blade attachments 320, 340 along the longitudinal direction L when the blade is connected to the saw 100. In order the cut an object, the first and second blades 220, 240 are configured to attach to the saw 100 so as to oscillate about a similar axis, or alternatively, about a different axes. For instance, the first and second blades 220 and 240 can oscillate about an axis that is perpendicular to a plane defined by any of the respective surfaces of each respective blade, such that the blades oscillate in an oscillation direction O. As further detailed below, the first and second blades 220, 240 oscillate in opposite directions.

Blades 220, 240 can be removably connected to the saw 100 by blade attachments 320, 340 which are configured to hold the blades 220, 240 in parallel planes that extend along the longitudinal direction L. The blade attachments 320, 340 each have a first pair of arms 320a and 320b and a second pair of arms 340b, 340b (FIGS. 1C and 4B) which surround the eccentric shaft 140 (see also FIG. 1C). The eccentric shaft 140 is disposed along a transverse direction T, which is perpendicular to the blades 220, 240 and the blade attachments 320, 340. The gearing is provided between the drive location and the first and second blades 220,240 to reduce the speed of oscillation of the blades 220,240. The gearing can include one or both of a planetary gear 120 and a 90° gear transmission 130.

In use, torque is transferred from the drive 110 via the planetary gear 120 and the 90° gear transmission 130 to rotate the eccentric shaft 140 about a central shaft axis 140a. As the shaft 140 rotates it converts rotational movement from the drive 110 to oscillation of the blades 220, 240 via the blade attachments 320 and 340. The blade attachments 320 and 340 define respective central axes 329 and 339 that are spaced from the central shaft axis 140a, and can be disposed opposite each other such that the central shaft axis 140a is disposed between the central axes 329 and 339. The eccentric shaft 140 is configured such that, as it rotates, it moves the first pairs of arms 320a and 320b, and a second pair of arms 340a and 340b of the attachment mechanism in opposite directions, thus oscillating the blades in opposite directions O relative to one another. The eccentric shaft 140 has a central portion 150, a first offset portion 152, and a second offset portion 154. The central portion 150 extends along the central shaft axis 140a. The first offset portion 152 second offset portions 154 extend along respective central offset axes (not shown) that lie in a similar plane with respective the central axes 339 and 329. The first pairs of arms 320a and 320b attach to the offset portion 154 and the second pair of arms 340a and 340b attach to offset portion 152. The blades 220, 240 are attached to the saw such that blades oscillate about the same axis, for instance the central shaft axis 140a, that extends along the transverse direction T. For instance, the central shaft axis 140a can extend along the transverse direction T and is substantially perpendicular to the first blade surfaces 256 and 258, and/or the second blade surfaces 356 and 358. The blades 220, 240 are securely connected to the blade attachments 320, 340, as described below, such that torque is transferred from the drive to the blades 220 and 240.

The planetary gear 120 achieves a reduction of the speed of the drive transmitted to the blades, and conversely an increase in torque. The ratio of reduction of speed along a direction from the drive 110 to the blades 220, 240 caused by the planetary gear is 1:3.9474, though it should be appreciated that the reduction of speed caused by the planetary gear can be configured as desired, for example between 1:1.1 and 1:10. The 90° gear transmission 130 can include a first or input gear 131, which can be a bevel gear, and a second or output gear 133, which can be a bevel gear, that is intermeshed with the first gear 131. The planetary gear 120 can be disposed between the drive location (and thus the motor drive 110) and the 90° gear transmission 130. The 90° gear transmission can be disposed between the planetary gear 120 and the eccentric shaft 140.

During operation, the first gear 131 rotates about a first axis of rotation 331 (FIG. 1A), and the second gear 133 rotates about a second axis of rotation 333 that is angularly offset, for instance oriented substantially 90°, with respect to the first axis of rotation 331. The first gear 131 is coupled to the drive 110 and configured to be driven to rotate by the drive 110 along the first axis of rotation, and the second gear 133 is coupled to the shaft 140, so as to drive the shaft to rotate about a corresponding axis of rotation that can be parallel or coincident with the second axis of rotation. Thus, the first gear 131 is disposed between the second gear 133 and the drive 110, and the second gear 133 is disposed between the shaft 140 and the first gear 131. The second gear 133 is configured to drive the eccentric shaft 140 to rotate, thereby causing the blades 220, 240 to reciprocally oscillate. The first gear 131 can be sized smaller than the second gear 133, and thus can have fewer teeth than the second gear 133. Accordingly, the second gear 133 rotates at a speed that is less than that of the first gear 131, and at a torque that is proportionally greater than that of the first gear 131. In accordance with one embodiment, the gear ratio can be as desired, for instance between 1:1.1 and 1:2. In accordance with the illustrated embodiment, the gear ratio can be 1:1.3846. The gear reduction of the 90° gear transmission produces a corresponding reduction of speed that is equal to the gear ratio, and a corresponding increase in torque output that is equal to the gear ratio. When the ratio of reduction of speed of the planetary gear is 1:3.9474 and the ratio of reduction of speed of the 90° gear transmission is 1:1.3846, the powered saw 100 produces a ratio of reduction in speed from the drive 110 to the eccentric shaft 140 of approximately ratio 1:5.4656. Although a planetary gear is illustrated, it would also be possible to use a bevel gear in its place.

The planetary gear 120 acts to provide high torque to the blades 220, 240 at low speed. In this way, the blades can be operated at low speed but with high torque. The blades cut with torque, not speed, and less heat is transmitted to bone. In addition, because the cutting is performed by two blades that are oscillating in opposite directions about the same axis, for instance the central shaft axis 140a, there is no resulting vibration of the bone or countertorque transmitted to the handpiece 102. Since no counter-torque is transmitted to the handpiece, handling of the tool is made easier, resulting in a more precise cut. The entry speed of the saw blades is between 2000 to 3000 rpm.

In an alternative embodiment of the saw, the planetary or bevel gear may be omitted so that there is a direct drive between the 90° gear transmission 130 and the blades 220, 240. For instance, referring to FIG. 1B, the powered saw 100 defines a receptacle 111 that can provide the drive location. The receptacle 111 is configured to receive a drive, such as a motor drive, at the drive location, the drive operable to rotate at a desired speed and produce a corresponding torque output. The powered saw 100 can be devoid of the planetary gear illustrated in FIG. 1A, such that the speed and torque output from the motor drive is communicated to the first gear 131 of the 90° gear transmission 130. Thus, the first gear 131 can be driven to rotate at substantially the same speed as the motor drive at substantially the same torque as is output from the motor drive. As described above, the first gear 131 can be sized smaller than the second gear 133, and thus can have fewer teeth than the second gear 133. Accordingly, the second gear 133 rotates at a speed that is less than that of the first gear 131, and at a torque that is proportionally greater than that of the first gear 131. In accordance with one embodiment, the gear ratio can be as desired, for instance between and including approximately 1:1.1 and approximately 1:5, including approximately 1:1.3846, approximately 1:1.5, or any suitable alternative gear ratio as desired. The gear reduction of the 90° gear transmission 130 produces a corresponding reduction of speed that is equal to the gear ratio, and a corresponding increase in torque output that is equal to the gear ratio. Furthermore, in accordance with the embodiment illustrated in FIG. 1B, the gear ratio of the 90° gear transmission 130 can define the gear ratio, and thus the speed reduction and torque increase, between the motor drive and the blades.

The output speed of the oscillation of the blades 220, 240 can be between 7000 to 10000 rpm, including 8000 rpm to 10000 rpm. In accordance with one embodiment of the powered saw 100, the speed of oscillation of the blades can be 7000 rpm.

The blades 220, 240 and the corresponding blade attachments 320, 340 may be symmetrical. Therefore, a saw 100 is provided that can have two identically configured blades. It should be appreciated that the blades can have different configurations as needed. For purpose of illustrating the configuration of first and second blades 220 and 240, only blade 220 will be further detailed below. It should be appreciated that the features described herein with respect to the first blade 220 are applicable to the second blade 240. Further, the features described herein regarding the blade attachment 320 are applicable to the blade attachment 340.

Figure 2:
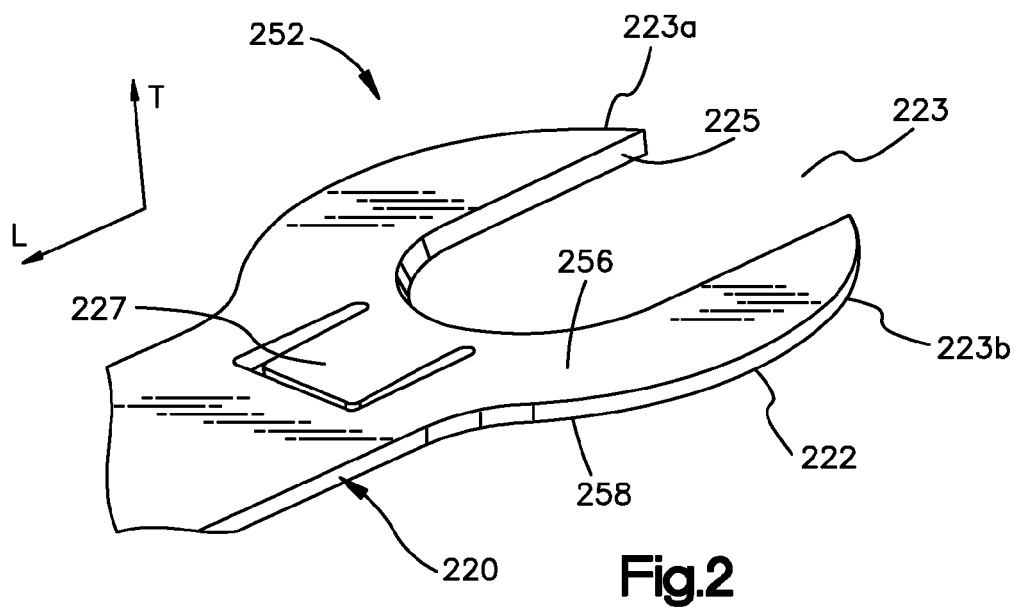
FIG. 2 is a perspective view of a proximal end of a saw blade according to an embodiment of the present disclosure.
Figure 3:
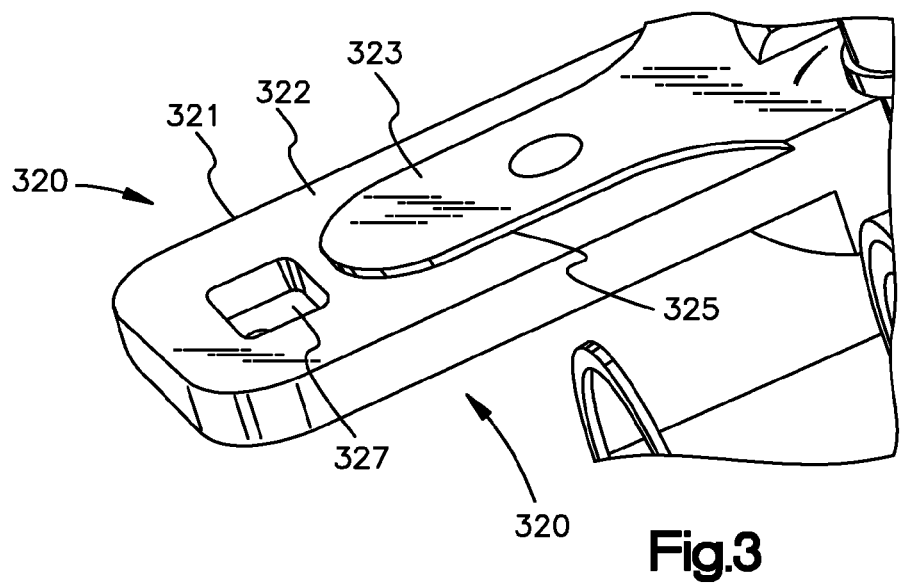
FIG. 3 is a perspective view of a mounting member according to an embodiment of the present disclosure.
Figure 6:
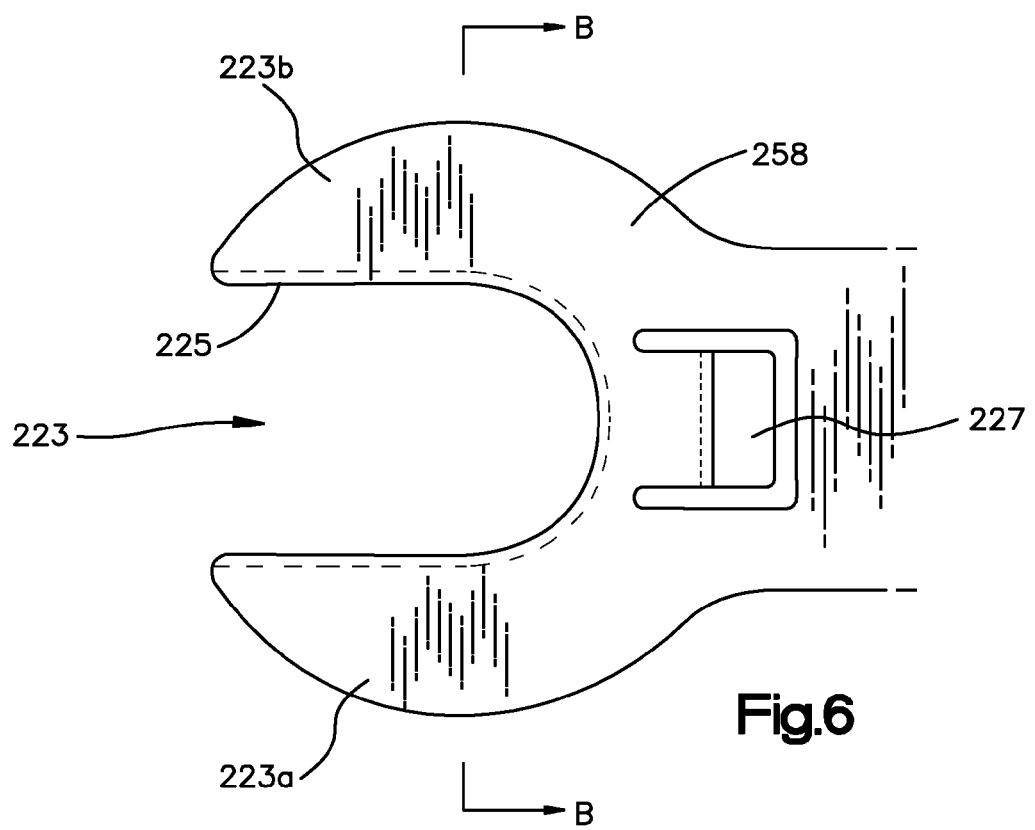
FIG. 6 is a bottom plan view of the proximal end of a saw blade shown in FIG. 2.

Referring to FIGS. 2, 3 and 6, the proximal end 252 of the blade 220 a spanner shaped head 222. The spanner shaped head 222 defines an opening 223 that extends along a longitudinal direction L. For instance, the head 222 has two arms 223a and 223b that are spaced apart and extend substantially parallel with respect one another. The arms 223a and 223b at least partially define and surround the opening 223. The proximal end 252 of the blade 220 also comprises a projection 227 that extends from the surface 258 (or 256) of blade 220 along a transverse direction T. The projection 227 can be a latch which is milled out from the blade 220 and is bent downwards along the transverse direction T so that it is resiliently biased into a position in which it extends from the surface 258 of the blade 220.

Figure 4A:
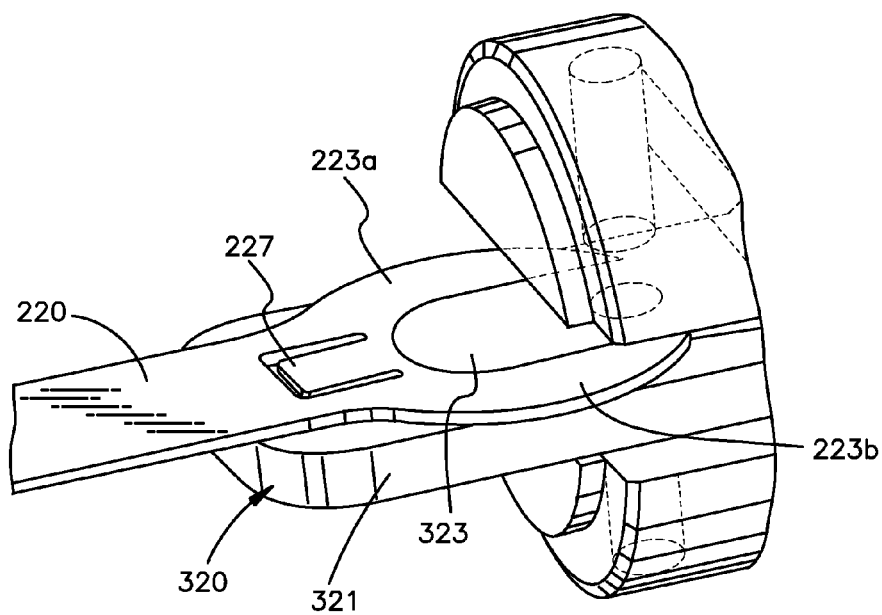
FIG. 4A is a cut away perspective view of the connection mechanism according to an embodiment of the present disclosure, illustrating the blade shown in FIG. 2 engaged with connection mechanism shown in FIG. 3.

Referring to FIG. 3, the blade attachment 320 includes a mounting member 321, for instance a mounting portion 321. The mounting portion 321 has a receiving surface 322, and a raised portion 323, for instance a portion that raised relative to the receiving surface 322 along the transverse direction T. The raised portion 323 is configured to correspond to the shape of the opening 223 of blade 220 shown in FIG. 2. The blade 220 can thus be slid into engagement with the receiving surface 322 such that the arms 223a and 223b surround the raised portion 323 of the mounting portion 321 (FIG. 4A) as shown in FIG. 4.

Figure 4B:
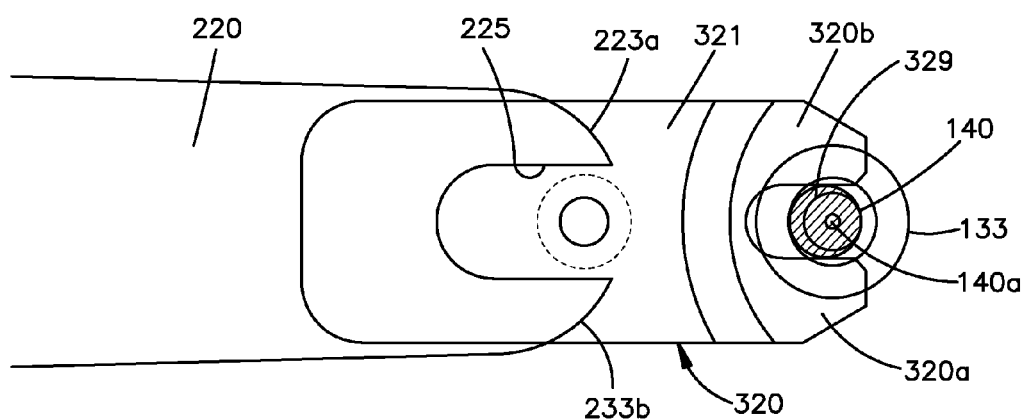
FIG. 4B is a bottom plan view of the connection mechanism illustrated in FIG. 4A.
Figure 5:
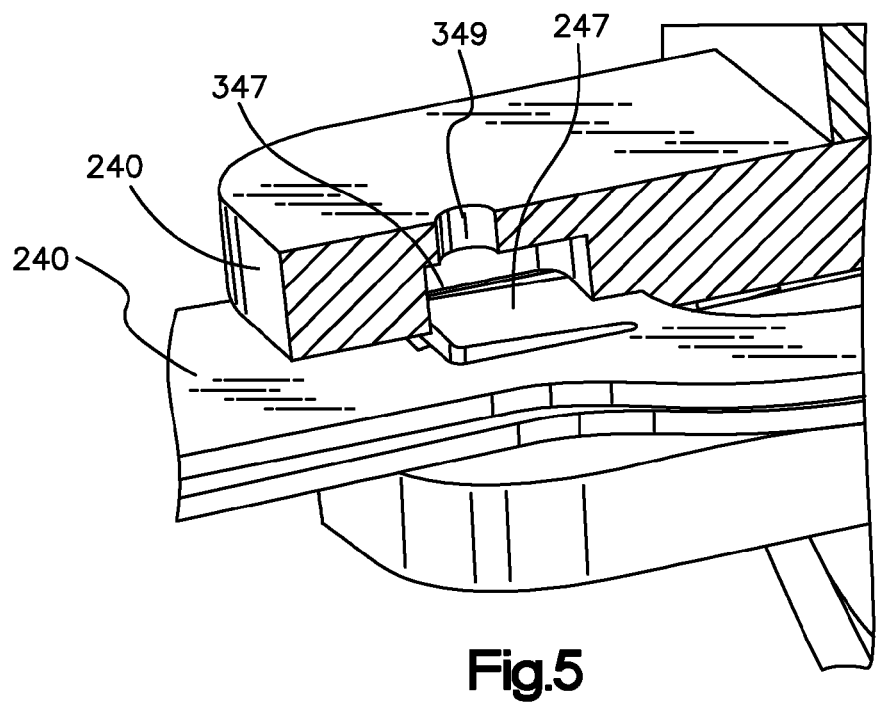
FIG. 5 is a sectional perspective view of a portion of connection mechanism according to an embodiment of the present disclosure.
Figure 7:
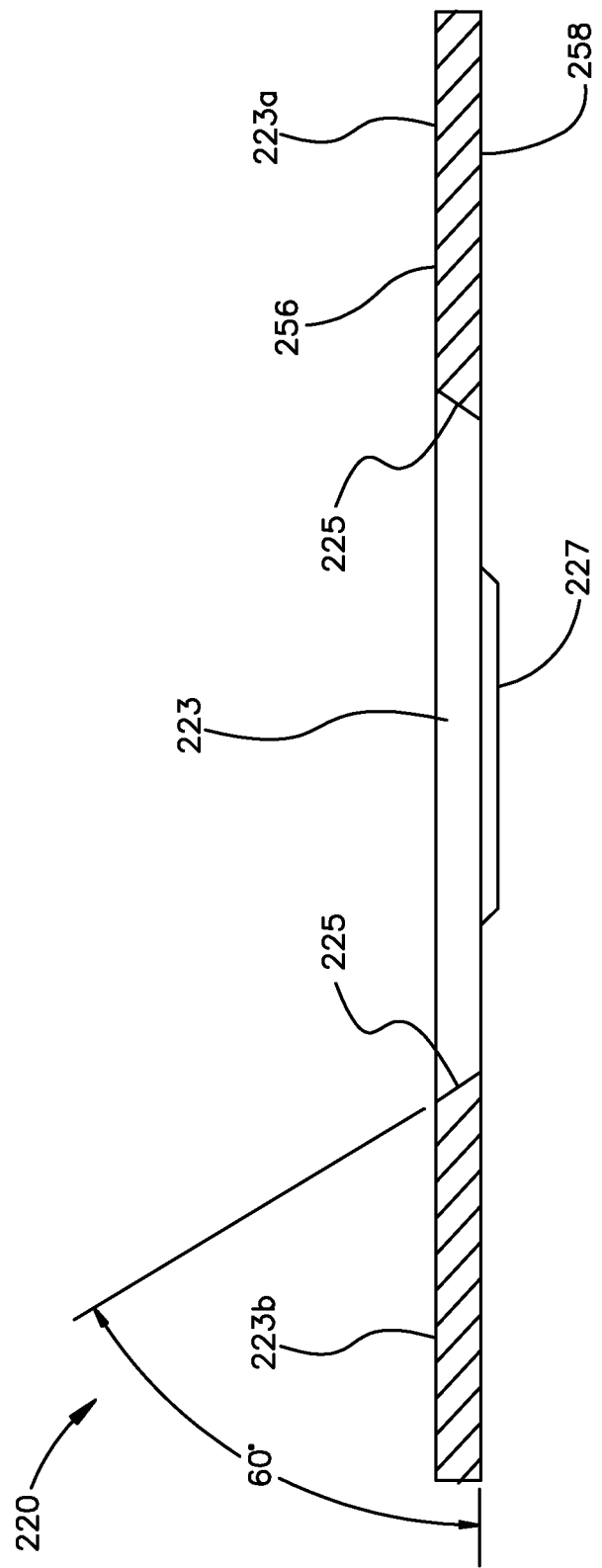
FIG. 7 is a cross-section of the proximal end of the saw blade along the line B-B in FIG. 6.

Referring to FIGS. 2, 6 and 7, the blade 240 can define an inner surface 225, the at least partially defines the opening 223. The inner surface 225 can extend from the upper blade surface 256 to the lower blade surface 258, and along the spaced apart arms 223a and 223b to define a U-shape. The inner surface 225 of arms 223a, 223b of the blade 220 are angled relative to the lower surface 258, or plane of the blade 220. In an embodiment, the angle of the inner surface 225 relative to the plane of the blade is about 60°. As can be seen in FIG. 3, the mounting portion 321 can also define an outer surface 325 that extends from the raised portion 323 to the receiving surface 322. The outer surface 325 of the raised portion 323 is angled relative the raised portion 323 to define a complementarily angle with respect to the inner surface 225 of blade 220. Thus, the outer surface 325 of the raised portion 323 and the inner surface 225 of the arms 223a and 223b interlock when the blade opening 223 is slid into close engagement with the raised portion 323 as shown in FIGS. 4A-B. As a result, movement relative to the surface of the blade is effectively prevented so that vibration between the two blade surfaces is minimized Referring to FIGS. 2 and 3, the receiving surface 322 has an aperture 327 that is positioned distal to the raised portion 323 along the longitudinal direction L. The aperture 327 is configured to receive at least a portion of the projection 227. The aperture 327 can act as a latching surface, against which the projection 227 of the blade 220 latches once the blade 220 has been slid into the position shown in FIGS. 4A-B. From this position, the blade 220 cannot be moved axially, for instance, along the longitudinal direction L out of engagement with the mounting portion 321. The latching projection 227 is resiliently biased towards the latching surface. However, the latching projection 227 is accessible through the aperture 327 by means of an opening in the opposing side of the mounting portion 321 to the receiving surface 322 (see for example opening 349 in FIG. 5). As a result, it is possible to release the latching projection 227 from its first position in the aperture 327 into which it is resiliently biased as shown in FIG. 4A and 4B, into a second position in which the projection 227 no longer latches against the latching surface. When projection is in the second position, the blade 220 is no longer prevented from moving axially relative to the mounting portion 321 and can be moved out of engagement therewith. Thus, the blade 220 is readily removable from engagement with the mounting member 321, and thus, the powered saw 100. As shown in FIG. 5, the second blade 240 can have a latching projection 247 which can engage the aperture 347 of the blade attachment 340.

It will of course be understood that the present disclosure has been described above purely by way of example, and that modifications of detail can be made within the scope of the present disclosure.

What is claimed:

1. A saw, comprising:
   a drive;
   a first blade configured to oscillate about a first axis, perpendicular to a plane defined by a surface of the first blade;
   a second blade configured to oscillate about a second axis, perpendicular to a plane defined by a surface of the second blade, in a direction opposite to that of the first blade;
   a gearing disposed between the drive and the first and second blades, the gearing configured to reduce the speed transmitted from the drive to the first and second blades; and
   an eccentric drive shaft rotatably connected to the drive, wherein the eccentric drive shaft acts to cause the first and second blades to oscillate.

2. A saw according to claim 1, wherein the eccentric drive shaft is perpendicular to the plane of each of the first and second blades.

3. A saw according to claim 2, wherein the gearing comprises a 90° gear transmission such that the drive is substantially parallel with the plane.

4. A saw according to claim 3, wherein the gearing provides a gear ratio of approximately 1:1.5.

5. A saw according to claim 4, further comprising a drive location that defines a receptacle configured to receive the drive.

6. A saw according to claim 1, wherein the speed of oscillation of the first and second blades is between 7000 to 10000 rpm.

7. A saw according to claim 4, wherein the speed of oscillation of the first and second blades is between 8000 and 10000 rpm.

8. A saw according to claim 4, wherein the speed of oscillation of the first and second blades is about 7000 rpm.

9. A saw, comprising:
   a drive;
   a first blade configured to oscillate about a first axis, perpendicular to a plane defined by a surface of the first blade;
   a second blade configured to oscillate about a second axis, perpendicular to a plane defined by a surface of the second blade, in a direction opposite to that of the first blade; and
   a gearing disposed between the drive and the first and second blades, the gearing configured to reduce the speed transmitted from the drive to the first and second blades, wherein the gearing comprises at least one of planetary and a 90° gear transmission.

10. A saw according to claim 9, wherein the gearing comprises the 90° gear transmission that includes a first bevel gear configured to be coupled to a drive, a second bevel gear that is coupled to the eccentric drive shaft, the first bevel gear having fewer teeth than the second bevel gear.

11. A saw according to claim 9, wherein the gearing comprises the 90° gear transmission, and the 90° gear transmission provides a gear ratio of 1:1.3846.

12. A saw according to claim 9, wherein the gearing comprises the planetary gear transmission and the 90° gear transmission, wherein the planetary gear transmission is disposed between the drive and the 90° gear transmission.

13. A saw according to claim 12, wherein the planetary gear defines a gear ratio of 1:3.9474 that defines a reduction of speed along a direction from the drive to the first and second blades.

14. A saw according to claim 13, wherein the speed of oscillation of the first and second blades is between 2000 to 3000 rpm.

15. A saw according to claim 1, wherein the first axis is coaxial with the second axis.

16. A saw according to claim 1, wherein the first and second blades are removably attached to the saw.

17. A saw according to claim 1, wherein in the saw is designed to cut bone.

18. A saw according to claim 1, wherein the drive is a motor drive.

19. A saw, comprising:
   a drive;
   a first blade configured to oscillate about a first axis, perpendicular to a plane defined by a surface of the first blade;
   a second blade configured to oscillate about a second axis, perpendicular to a plane defined by a surface of the second blade, in a direction opposite to that of the first blade; and
   a gearing disposed between the drive and the first and second blades, wherein the saw is configured to reduce the speed transmitted from the drive to the first and second blades by reducing the speed at the gearing.

20. A saw according to claim 19, further comprising an eccentric drive shaft rotatably connected to the drive, wherein the eccentric drive shaft acts to cause the first and second blades to oscillate.

21. A saw according to claim 20, wherein the eccentric drive shaft is perpendicular to the plane of each of the first and second blades.

22. A saw according to claim 21, wherein the gearing comprises a 90° gear transmission such that the drive is substantially parallel with the plane.

23. A saw according to claim 22, wherein the gearing provides a gear ratio of approximately 1:1.5.

24. A saw according to claim 23, further comprising a drive location that defines a receptacle configured to receive the drive.

25. A saw according to claim 19, wherein the speed of oscillation of the first and second blades is between 7000 to 10000 rpm.

26. A saw according to claim 25, wherein the speed of oscillation of the first and second blades is between 8000 and 10000 rpm.

27. A saw according to claim 25, wherein the speed of oscillation of the first and second blades is about 7000 rpm.

28. A saw according to claim 19, wherein the gearing comprises at least one of a planetary and a 90° gear transmission.

29. A saw according to claim 28, wherein the gearing comprises the 90° gear transmission that includes a first bevel gear configured to be coupled to a drive, a second bevel gear that is coupled to the eccentric drive shaft, the first bevel gear having fewer teeth than the second bevel gear.

30. A saw according to claim 28, wherein the gearing comprises the 90° gear transmission, and the 90° gear transmission provides a gear ratio of 1:1.3846.

31. A saw according to claim 28, wherein the gearing comprises the planetary gear transmission and the 90° gear transmission, wherein the planetary gear transmission is disposed between the drive and the 90° gear transmission.

32. A saw according to claim 31, wherein the planetary gear defines a gear ratio of 1:3.9474 that defines a reduction of speed along a direction from the drive to the first and second blades.

33. A saw according to claim 32, wherein the speed of oscillation of the first and second blades is between 2000 to 3000 rpm.

\* \* \* \* \*